US011275072B2

(12) United States Patent
Evans et al.

(10) Patent No.: US 11,275,072 B2
(45) Date of Patent: Mar. 15, 2022

(54) EFFECTS OF OXYGEN ON GREASE

(71) Applicants: Jonathan C. Evans, Midland, MI (US);
Theodore W. Selby, Midland, MI (US);
Marta Manning, Midland, MI (US)

(72) Inventors: Jonathan C. Evans, Midland, MI (US);
Theodore W. Selby, Midland, MI (US);
Marta Manning, Midland, MI (US)

(73) Assignee: TANNAS COMPANY, Midland, MI (US)

( * ) Notice: Subject to any disclaimer, the term of this patent is extended or adjusted under 35 U.S.C. 154(b) by 69 days.

(21) Appl. No.: 15/731,004

(22) Filed: Apr. 5, 2017

(65) Prior Publication Data

US 2017/0284994 A1    Oct. 5, 2017

Related U.S. Application Data

(63) Continuation-in-part of application No. 14/121,952, filed on Nov. 6, 2014, now Pat. No. 10,914,719.
(Continued)

(51) Int. Cl.
*G01N 33/28* (2006.01)
*C10M 109/00* (2006.01)
(Continued)

(52) U.S. Cl.
CPC ....... *G01N 33/2805* (2013.01); *C10M 109/00* (2013.01); *C10M 113/06* (2013.01);
(Continued)

(58) Field of Classification Search
CPC ............ G01N 33/2805; C10M 109/00; C10M 169/02; C10M 113/06; C10M 121/04; C10N 2240/10
See application file for complete search history.

(56) References Cited

U.S. PATENT DOCUMENTS 7,678,328 B1    3/2010 Secrist et al.
8,679,405 B1    3/2014 Secrist et al.
(Continued)

OTHER PUBLICATIONS

USPTO Patent Full-Text and Image Database, Patent Database Search Results, ACLM/about, Hits 1 through 50 of 1241466, Aug. 7, 2018 A.D.
(Continued)

*Primary Examiner* — Rebecca M Fritchman
(74) *Attorney, Agent, or Firm* — Christopher John Rudy

(57) ABSTRACT

Effects of Oxygen on grease or another organic paste product can be evaluated with a modified version of the ASTM D942 test methodology for oxidation stability of lubricating greases or other organic paste products by employment of an oxidation pressure vessel, in which at least one of (A) a very small sample of the grease or other organic paste product is deployed for testing within the oxidation pressure vessel such that the sample has an enhanced surface area to mass ratio, and (B) a temperature other than about 99° C. is employed during the testing. In general, the testing is carried out under oxidation pressure conditions. The sample may be evaluated with respect to Oxygen uptake. Additional technique(s) directed to oxidation and/or other properties of the sample may be carried out before to after any Oxygen uptake evaluation, for example, FTIR analysis and/or ATR-FTIR analysis.

21 Claims, 4 Drawing Sheets

Related U.S. Application Data

(60) Provisional application No. 62/390,774, filed on Apr. 8, 2016, provisional application No. 61/965,160, filed on Jan. 24, 2014, provisional application No. 61/962,464, filed on Nov. 7, 2013.

(51) Int. Cl.
    *C10M 121/04*    (2006.01)
    *C10M 169/02*    (2006.01)
    *C10M 113/06*    (2006.01)
    *G01N 33/00*     (2006.01)
    *G01N 21/35*     (2014.01)
    *C10N 40/25*     (2006.01)

(52) U.S. Cl.
    CPC ........ *C10M 121/04* (2013.01); *C10M 169/02* (2013.01); *G01N 33/2888* (2013.01); *C10N 2040/25* (2013.01); *G01N 21/35* (2013.01); *G01N 2021/3595* (2013.01)

(56) References Cited

U.S. PATENT DOCUMENTS

| | | | |
|---|---|---|---|
| 8,975,083 B2 | 3/2015 | Selby et al. | |
| 2003/0157725 A1* | 8/2003 | Franzen | G01N 21/552 436/171 |
| 2017/0205355 A1 | 7/2017 | Selby et al. | |

OTHER PUBLICATIONS

USPTO Patent Full-Text and Image Database, Patent Database Search Results, ACLM/predetermined, Hits 1 through 50 of 1036615, Aug. 7, 2018 A.D.
USPTO Patent Full-Text and Image Database, Patent Database Search Results, ACLM/"very small," Hits 1 through 50 of 2152, Aug. 7, 2018 A.D.
Evans et al., U.S. Appl. No. 62/390,774, filed Apr. 8, 2016. This discloses oxidation of grease, and is a domestic priority document cited on p. 1 of the present specification.
Selby et al., U.S. Appl. No. 14/121,952, filed Nov. 6, 2014. This discloses grease oxidation, the parent of which the present application is a continuation-in-part, and is cited on pp. 1 and 3 of the present specificatiion. This parent is projected for publication on Jul. 20, 2017, and published as US 2017/0205355 A1 on that date.
Selby et al., U.S. Appl. No. 61/962,464, filed Nov. 7, 2013. This discloses grease oxidation, is also a domestic priority document of the parent, hence hereof, and is cited on p. 1 of the present specification.
Selby et al., U.S. Appl. No. 61/965,160, filed Jan. 24, 2014. This discloses grease oxidation, is a domestic priority document of the parent, hence hereof, and is cited on p. 1 of the present specification.
ASTM International, ASTM D942-15, Standard Test Method for Oxygen Stability of Lubricating Greases by the Oxygen Pressure Vessel Method, Jun. 2015. Iterations of this are cited on pp. 1-10 of the present specification.
Panchal et al., *Ind. Crops Prod.*, vol. 63, pp. 48-52, 2015. This discloses bio-based grease, a value added product from renewable resources, and is cited on p. 1 of the present specification.
Schneider, *J. Sci. Food Agric.*, vol. 86, pp. 1769-1780, 2006. This discloses plant-oil based lubricants and hydraulic fluids, and is cited on p. 1 of the specification.
Kimura et al., *J. Synth. Lubr.*, vol. 20, pp. 241-255, 2003. This discloses properties and applications of synthetic greases, and is cited on p. 2 of the specification.
Fish, 82$^{nd}$ NLGI Annual Meeting, Coeur d'Alene, Idaho, U.S.A., Jun. 6, 2015. This discloses the development of more environmentally considerate greases, and is cited on p. 2 of the present specification.
Kumar et al, *NLGI Spokesman*, vol. 78, No. 5, pp. 24-35, 2014. This discloses challenges in manufacturing of bio-based greases, and is cited on p. 2 of the present specification.
Wilkinson et al., *NLGI Spokesman*, vol. 79, No. 2, pp. 6-9, 2015. This discloses meeting the challenges posed by environmentally acceptable lubricants, and is cited on p. 2 of the present specification.
ASTM International, ASTM D2266-01 (Reapproved 2015), Standard Test Method for Wear Preventive Characteristics of Lubricating Grease (Four-Ball Method), Jun. 2015. This is cited, in general, on p. 2 of the present specification.
ASTM International, ASTM D2509-14, Standard Test Method for Measurement of Load-Carrying Capacity of Lubricating Grease (Timken Method), Feb. 2015. This is cited, in general, on p. 2 of the present specification.
ASTM International, ASTM D2596-15, Standard Test Method for Measurement of Extreme-Pressure Properties of Lubricating Grease (Four-Ball Method), Sep. 2015. This is cited, in general, on p. 2 of the present specification.
Secrist et al., U.S. Pat. No. 7,678,328 B1, Mar. 16, 2010. This discloses a rotatable bomb, and is cited on pp. 1-2 of the present specification.
Secrist et al., U.S. Pat. No. 8,679,405 B1, Mar. 25, 2014. This is a division of the '328 patent, discloses a rotatable bomb, and is cited on pp. 1-2 of the specification.
Selby et al., U.S. Pat. No. 8,975,083 B2, Mar. 10, 2015. This discloses oil life measurement, and is cited on pp. 1-2 of the present specification.
Secrist et al., U.S. Appl. No. 60/527,725, filed Dec. 8, 2003. This is the domestic priority document of the '328 and '405 patents, discloses a rotatable bomb, and is cited on pp. 1-2 of the present specification.
Selby et al., U.S. Appl. No. 61/795,088, filed Oct. 10, 2012. This is the domestic priority document of the '083 patent, discloses oil life measurement, and is cited on pp. 1-2 of the present specification.
ASTM International, ASTM D2272-09, Standard Test Method for Oxidation Stability of Steam Turbine Oils by Rotating Pressure Vessel, Sep. 2009. This is cited, in general, on p. 3 of the present specification.
ASTM International, ASTM D4742-02a, Standard Test Method for *Oxidation Stability of Gasoline Automotive Engine Oils by Thin-Film Oxygen Uptake*, Jul. 2002. This is cited, in general, on p. 3 of the present specification.
Selby et al., "Comparative Study of Grease Oxidation Using an Advanced Bench Test Technique," Proceedings of the 19$^{th}$ International Colloquium Tribology—Lubricants, Materials and Lubrication, Technische Akademie Esslingen, Esslingen, Germany, Jan. 22, 2014. This is cited on p. 6 of the present specification.
Azad et al., "An Advanced Technique for Grease Oxidation Measurement," *NLGI Spokesman*, vol. 78, No. 6, pp. 30-40, 2015. This is cited on p. 6 of the present specification.
Nagendramma et al., *Lubricants*, 2015, 3, 628-636. This discloses eco-friendly multipurpose lubricating greases from vegetable residual oils.
Evans et al., U.S. Appl. No. 62/390,774, filed Apr. 8, 2016 A.D., "Oxidation of Grease."
Selby et al., U.S. Appl. No. 14/121,952, filed Nov. 6, 2014 A.D., "Grease Oxidation."
Selby et al., U.S. Appl. No. 61/962,464, filed Nov. 7, 2013 A.D., "Grease Oxidation."
Selby et al., U.S. Appl. No. 61/965,160, filed Jan. 24, 2014 A.D., "Grease Oxidation."
ASTM International, ASTM D942-15, Jun. 2015.
Panchal et al., *Ind. Crops Prod.*, vol. 63, pp. 48-52, 2015.
Schneider, *J. Sci. Food Agric.*, vol. 86, pp. 1769-1780, 2006.
Kimura et al., *J. Synth. Lubr.*, vol. 20, pp. 241-255, 2003.
Fish, 82nd NLGI Annual Meeting, Coeur d'Alene, Idaho, Jun. 6, 2015.
Kumar et al., *NLGI Spokesman*, vol. 79, No. 2, pp. 6-9, 2015.
ASTM Internatiional, ASTM D226-01 (Reapproved 2015), Jun. 2015.
ASTM International, ASTM D259-14, Feb. 2015.
ASTM International, ASTM D2596-15, Sep. 2015.
Secrist et al., U.S. Appl. No. 60/527,725, filed Dec. 8, 2003 A.D., "Rotatable Bomb."

(56) References Cited

OTHER PUBLICATIONS

Selby et al., U.S. Appl. No. 61/795,088, filed Oct. 10, 2012 A.D., "Oil Life Measurement."
ASTM Internationa, ASTM D2272-09, Sep. 2009.
ASTM International, ASTM D4742-02a, Jul. 2002.
Selby et al., Proceedings of the 19th International Colloquium Tribology—Lubricants, Materials and Lubrication, Technische Akademie Esslingen, Esslingen, Germany, Jan. 22, 2014, "Comparative Study of Grease Oxidation Using and Advance Bench Test Technique."
Azad et al., NLGI Spokeman, vol. 78, No. 6, pp. 30-40, 2015.
Nagendramma et al., *Lubricants*, 2015, 3, 628-636.

* cited by examiner

EFFECTS OF OXYGEN ON GREASE

This claims benefits under 35 USC 119(e) of provisional application No. U.S. 62/390,774 filed on Apr. 8, 2016 A.D., and under 35 USC 120 as a continuation-in-part of nonprovisional U.S. application Ser. No. 14/121,952 filed on Nov. 6, 2014 A.D., which, as does the present application through U.S. application Ser. No. 14/121,952, claims benefits under 35 USC 119(e) of provisional application Nos. U.S. 61/962,464 filed on Nov. 7, 2013 A.D. and U.S. 61/965,160 filed on Jan. 24, 2014 A.D. The specifications of those applications, to include drawings, are incorporated herein by reference in their entireties.

FIELD AND PURVIEW OF THE INVENTION

In general, this concerns a method for evaluating effects of Oxygen on grease and other organic paste products. For example, oxidation effects may be evaluated. It is an advancement over the ASTM D942 test method and methodology disclosed in the '952 application of Selby et al., which itself advances the ASTM D942 grease oxidation test. A very small sample size and/or a temperature other than about 99° C. are employed.

BACKGROUND TO THE INVENTION

Grease-like lubricants from animal fats and the alkaline components of fire-place ash are believed to be the earliest form of man's lubrication for his wooden wheel-and-shaft vehicles. First records noted use in Egypt of such materials blended with lime to lubricate chariots. After thousands of years, as the $19^{th}$ century came to a close, fat- and vegetable-based greases were replaced with more easily manufactured and durable mineral oil based greases. Yet, bio-based greases derived from plant oil feedstock tend to have excellent tribological properties and generally have very high viscosities and flash points. They have some inherent disadvantages, however, such as sensitivity to hydrolysis and oxidation. See, Panchal, T., et al., "Bio-based Grease, a Value Added Product from Renewable Resources," *Ind. Crops Prod.*, 2015, 63, 48-52.

Today's revival of bio-based greases is being driven by an increased global focus towards the use of ecologically-friendly, environmentally safe materials. It is estimated that some 50% of all lubricants worldwide end up in the environment because of total loss applications, volatility, spills or accidents. See, Schneider, M., "Plant-oil Based Lubricants and Hydraulic Fluids," *J. Sci. Food Agric.*, 2006, 86: 1769-1780. The introduction of legislation and consumer-driven initiatives such as the U.S. Environmental Protection Agency's Vessel General Permit, the European Union's Ecolabel scheme, and the U.S. Department of Agriculture's BioPreferred program has increased renewable and bio-sourced grease use. Such recent trends have primarily focused the grease industry on price and performance as well as biodegradability and ecological toxicity. See, Kimura, H., et al., "Properties and Applications of Synthetic Greases," *J. Synth. Lubr.*, 2003, 20, 241-255; Fish, G., "The Development of More Environmentally Considerate Greases," $82^{nd}$ NLGI Annual Meeting, Coeur d'Alene, Idaho, U.S.A., Jun. 6, 2015; Kumar, A., et al., "Challenges in Manufacturing of Bio-Based Greases," *NLGI Spokesman*, 2014, 78(5), 24-35; and Wilkinson, M., et al., "Meeting the Challenges Posed by Environmentally Acceptable Lubricants," *NLGI Spokesman*, 2015, 79(2), 6-9.

Of course, properties of a grease that sustain lubricating performance under operational stress and temperature are critical to the capability of the grease to minimize friction, reduce wear, increase system efficiency, and extend operating life of the grease as a lubricant. In assessing such properties and capabilities, various test methods and associated test machines are known. See, the ASTM D942 Oxygen pressure vessel method for oxidation stability of lubricating greases. See also, the ASTM D2266 four-ball test method for wear preventive characteristics of lubricating grease; the ASTM D2509 timken method for measurement of the load-carrying capacity of lubricating grease; and the ASTM D2596 four-ball method for measurement of extreme pressure properties of lubricating grease.

Although such methods are valuable, they are not without their drawbacks and shortcomings. For example, the ASTM D942 method, although generally long-used, having been introduced in 1947, even in a later iteration, ASTM D942-15, "Oxidative Stability of Lubricating Greases by the Oxygen Pressure Vessel Method," requires a lengthy period of time to complete. For instance, it may take a hundred hours or hundreds of hours of test time, after a lengthy set up time. Also, the ASTM D942 method is technically cumbersome and inexact, and requires a relatively large, 20.0-g sample, distributed evenly among five sample dishes. As well, developed so as to maintain quality control of grease production in manufacturing, the ASTM D942 method is limited as a laboratory investigative test for the evaluation of oxidation. Thus, it is clearly stated in Section 4.1 of ASTM D942-15 that that method should not be applied to compare the oxidative stability of the tested grease to actual behavior in service.

In improvements in another field, i.e., that of testing oils, patents to Secrist et al., U.S. Pat. Nos. 7,678,328 B1 and 8,679,405 B1, disclose a rotatable bomb, and Selby et al., U.S. Pat. No. 8,975,083 B2, discloses oil-life measurement—the specifications of those patents, along with their domestic priority applications, U.S. provisional application Nos. 60/527,725 filed on Dec. 8, 2003 A.D. and U.S. 61 61/795,088 filed on Oct. 10, 2012 A.D., incorporated herein by reference in their entireties, to include drawings. That art improves ASTM D2272 and ASTM D4742 test methodology, notably with instrumentation disclosed therein and embodied commercially as the Quantum® instrument from Tannas Company, Midland, Mich., U.S.A.

THE PARENT

The aforementioned '952 application of Selby et al., which is the parent hereto, discloses grease oxidation. It embraces a significantly improved version of the ASTM D942 test method, with apparatus employable to effect the same, the Quantum® instrument, which has electric heating of its pressure chamber, in essence being a liquid bath-free isothermal instrument, and is equipped with a pivotable, cradling framework, and accessories. There, the desirable simplicity and straightforward features of the ASTM D942 test method are retained, but its undesirable liquid bath and large sample size requirements are avoided. As well, the parent discloses use of small, 1-g samples per dish, with different greases in different dishes for a screening test, and such techniques as Fourier transform infra red (FTIR) analysis, and FTIR equipped with attenuated total reflectance (ATR) to extend application of the ASTM D942 method to comparative oxidation responses of greases.

As valuable as that technology is, and it is valuable indeed, it is not without its own shortcomings. These may relate to a more comprehensive ability to assess the extent of oxidation over time, to gain insight into the rate of oxidation, to assess the extent of oxidation penetration of a sample, and to compare the oxidative resistance of different greases.

SOME DESIDERATA

It would be desirable to improve upon the art of grease evaluation. It would be desirable, moreover, to ameliorate if not overcome drawbacks and shortcomings in the arts and fields such as set forth above. It would be desirable to provide the art of grease evaluation an alternative.

A FULL DISCLOSURE OF THE INVENTION

Provided hereby in address of the foregoing is a method for evaluating effects of Oxygen on grease or another organic paste product, which comprises a modified version of ASTM D942 test methodology for oxidation stability of lubricating greases or other organic paste products by employment of an oxidation pressure vessel, for example, ASTM D942-15 test methodology, in which at least one of (A) a very small sample of the grease or other organic paste product is deployed for testing within the oxidation pressure vessel such that the sample has an enhanced surface area to mass ratio, and (B) a temperature other than about 99° C. is employed during the testing. In general, the testing is carried out under oxidation pressure conditions. The sample can be evaluated with respect to Oxygen uptake. Additional technique(s) directed to oxidation and/or other properties of the sample may be carried out before to after any Oxygen uptake evaluation, for example, FTIR analysis and/or ATR-FTIR analysis.

The invention is useful in testing and evaluation of grease or other organic paste product.

Hereby, the art is advanced in kind, and an alternative is provided the art.

Thus, ASTM D942 type testing is further advanced, even over the advances of the parent. In particular, employment of the small sample sizes in the present methodology provides for a significant enhancement of oxidation and hence the potential for complete oxidation and/or for production of various oxidation products, and a significant decrease in test time. Furthermore, maintaining a fixed volume of Oxygen at an Oxygen-pressure of 110±2 pounds per square inch (psi) with a smaller sample size changes the sample-mass to Oxygen-volume ratio, resulting in more complete oxidation of the sample at a selected temperature. The effect of altering the test sample-mass to Oxygen-volume ratio for a sample can be investigated or confirmed by advanced techniques, for example, ATR-FTIR. As a result, an experimental approach used to further improve results from ASTM D942 type testing so as to sharpen understanding of grease oxidation resistance is provided. As well, improved oxidation uptake test data is coupled with modern spectral analysis, for example, infrared analysis, for more precise comparison of oxidation response where a grease or other organic paste product sample can be scanned in an un-oxidized state and compared to the sample in an oxidized state, say, from modified or unmodified ASTM D942 test methodology or from samples obtained from employment in the field. The present approach employs much less sample in the test in order to enhance oxidation throughout the sample and/or accommodate a relatively small volume, thus enabling generation of additional data points and/or employment of a limited amount of sample available from the field, for example, in a forensic examination. In addition, requiring much less sample than that required in ASTM D942 type testing, the present approach requires less time. Moreover, much valuable information can be gained by employing a temperature other than 99° C. in a test.

And so, a basic advance in instrumental analysis for assessing oxidation resistance is provided. For example, both mineral-based and ecology-friendly bio-based greases are capable of being evaluated, as well as are other grease lubricants and organic paste products. Since oxidation is one of the primary causes of lubricant degradation, a more effective and repeatable oxidation test is most important and provided hereby for both mineral and bio-based greases.

The present methodology can be employed in conjunction with other test protocols.

Numerous further advantages attend the invention.

Advantageously, in general, the sample for testing can be first exposed to high pressure oxidizing gas under an elevated temperature in a relatively new instrument for testing high Oxygen pressure and temperature oxidation of lubricants, the Quantum® instrument, which, as mentioned in the parent and above, was specially modified to provide a significantly advanced version of the widely-used ASTM D942 grease oxidation test that originated in 1947. After exposure, the grease sample can be evaluated as to the degree of depletion of Oxygen occurring in the test. Beneficially, at times before-to-after the exposure, the sample can be evaluated by sensitive FTIR and/or ATR-FTIR instrumentation analysis(es) as to the type and/or degree of oxidation and/or other effect(s) that may occur or may have occurred.

The very small sample can be of a size such as less than or substantially less than a 1-g individual dish sample (less than 5-g for five sample dishes) otherwise disclosed for a screening test in the parent application, and far less than required as in ASTM D942 type testing, to an about 0.5-g individual dish sample or less.

The temperature other than 99° C. for employment during the testing can be less than or greater than or substantially less and/or greater than 99° C., advantageously substantially greater than 99° C., to include about 110° C. or higher, about 120° C. or higher, about 130° C. or higher, about 150° C. or higher, about 175° C. or higher, about 200° C. or higher, and so forth, such as up to melting, evaporation, and/or decomposition of the sample. The temperature of testing may be centered around expected operating temperatures of the sample in the field.

The drawings form part of the specification hereof With respect to the drawings, which are not necessarily drawn to scale, the following is briefly noted:

Figure 7:
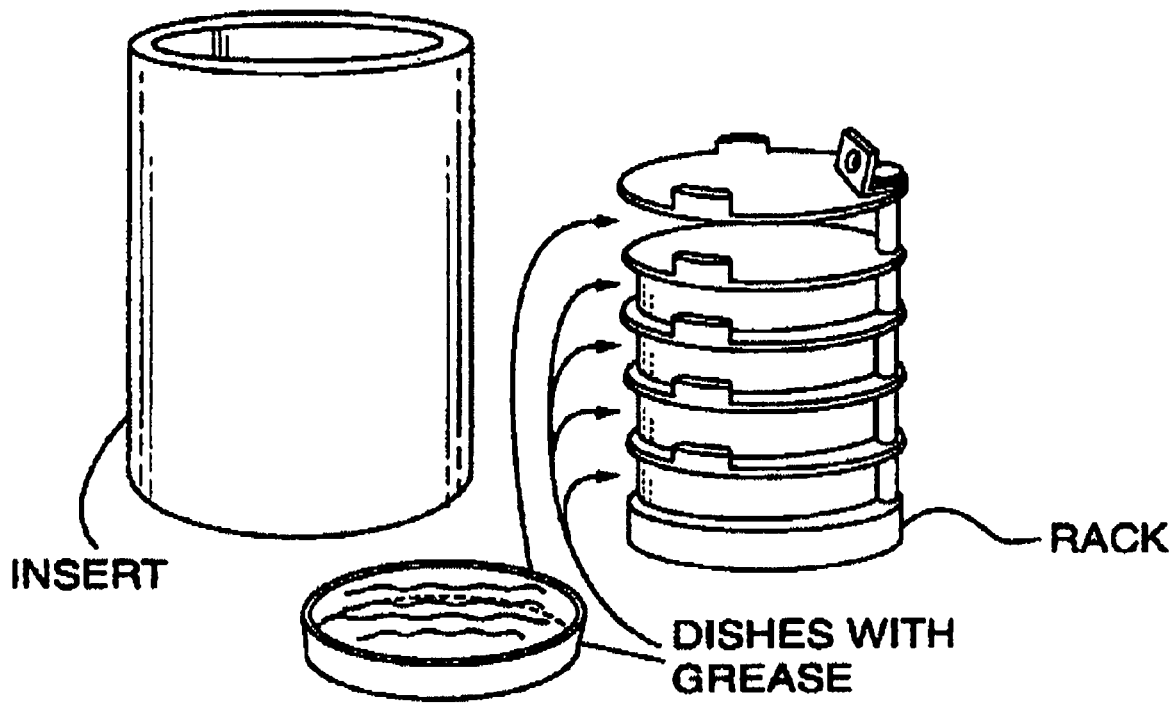

FIG. 7 is a perspective view of an insert, sample dishes, and a rack for the sample dishes found in parent U.S. application Ser. No. 14/121,952 for insertion into a rotatable bomb instrument found in U.S. Pat. Nos. 7,678,328 B1 and 8,679,405 B1 with cradling framework also found in the '952 parent application.

Figure 1:
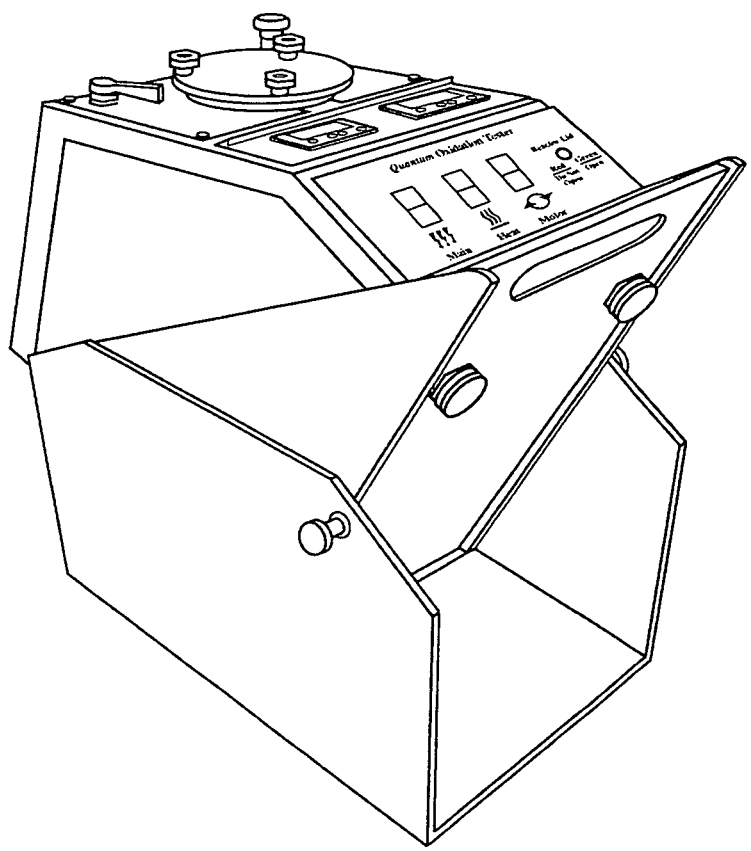
FIG. 1 is a perspective view of a Quantum® instrument positioned upright for ASTM D942 type testing, and testing according to the present methodology.
Figure 8:
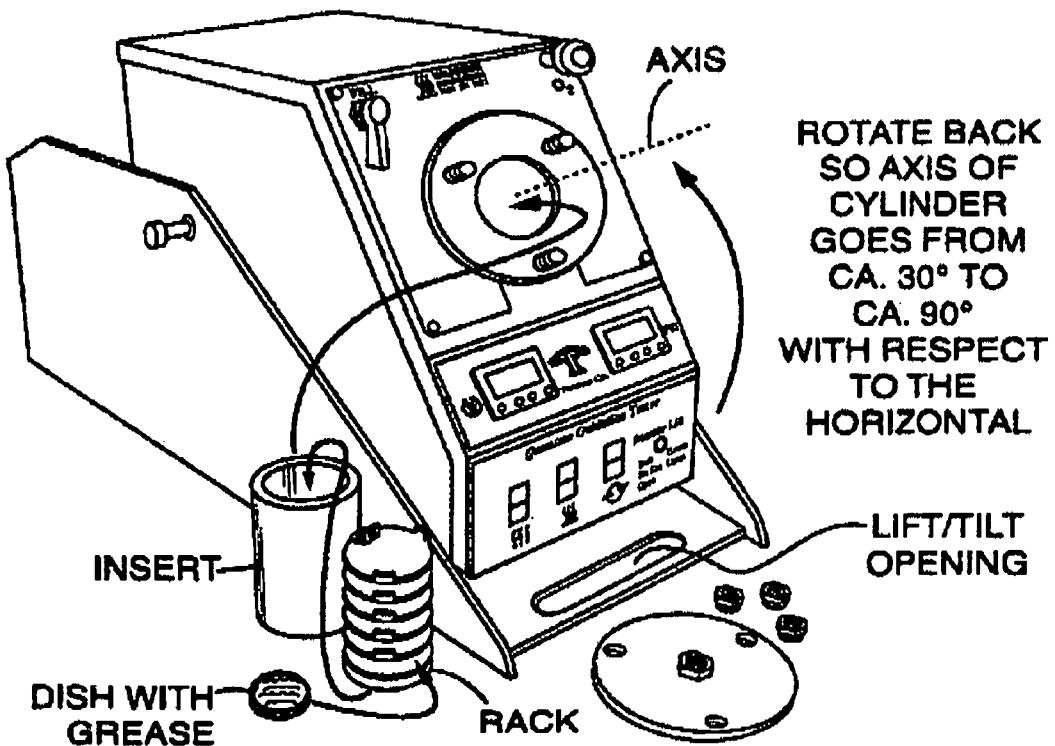

FIG. 8 is a perspective view of the insert, sample dishes, and rack found in the '952 parent application along with the rotatable bomb instrument found in the '328 and '405 patents and cradling framework also found in the '952 parent application that can be rotated back so that the axis of the cylinder of the rotatable bomb instrument is approximately 90° with respect to the horizontal as depicted in FIG. 1.

The invention can be further understood by the additional detail set forth below. As with the foregoing, the following, which also may be read in view of the drawings, is to be taken in an illustrative, and not necessarily limiting, sense.

Oxidation testing is exemplary of the invention.

OXIDATION TESTING

Oxidative resistance of six greases was initially evaluated by the ASTM D942-15 test method, which requires exposure of a 20-g grease sample to be tested distributed evenly in five glass dishes (4-g grease per dish) with an approximately 25-cm$^2$ exposed surface area per dish and, thus, 125-cm$^2$ surface area per 20-g sample per test. The dishes are stacked on a metal rack with an approximately 5-mm gap between the top of each stacked glass dish and the shelf above. The combined stack of grease-filled dishes is then inserted into a cylindrical pressure chamber and exposed to Oxygen of not less than 99.5% purity at an initial 100-psi (690-kPa) pressure and room temperature which is then increased to 99±0.5° C. Under this increased temperature, the Oxygen pressure is carefully released to maintain no more than 110±2 psi (758±14 kPa). The test is normally continued for a chosen period of one hundred to five hundred hours, and the resultant decrease in Oxygen pressure as a result of grease oxidation is taken as the test result.

As disclosed in the parent, the bath-free Quantum® instrument, modified as shown in FIG. 1 and operated under isothermal conditions, was used to perform the ASTM D942 grease oxidation testing. Compare with Selby, T., et al., "Comparative Study of Grease Oxidation Using an Advanced Bench Test Technique," Proceedings of the 19$^{th}$ International Colloquium Tribology Lubricants, Materials and Lubrication, Technische Akademie Esslingen, Esslingen, Germany, Jan. 22, 2014; Azad, S., et al., "An Advanced Technique for Grease Oxidation Measurement," *NLGI Spokesman,* 2015, 78(6), 30-40.

Figure 2:
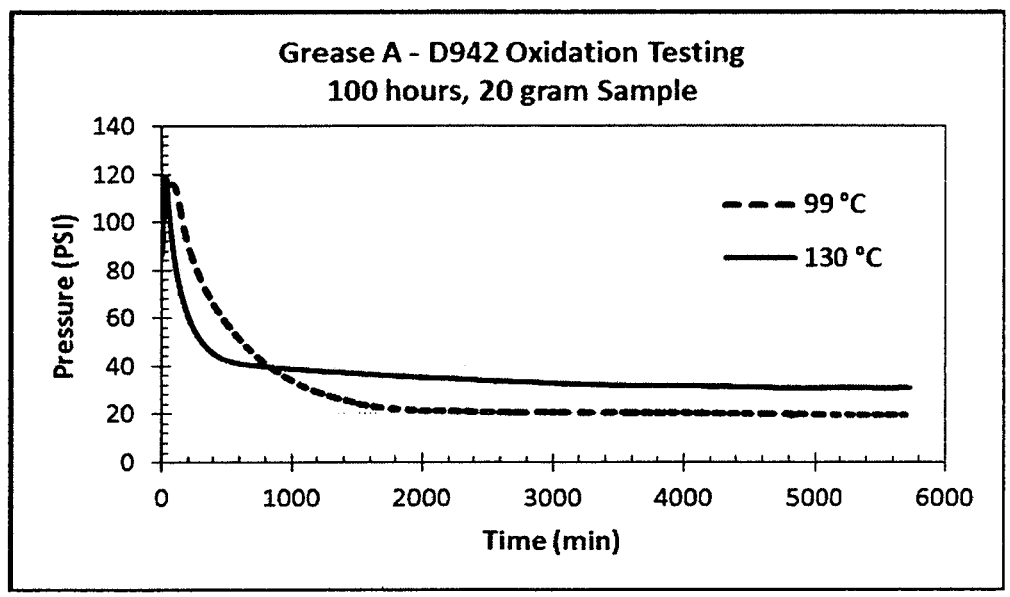
FIG. 2 is a graph of Grease A, ASTM D942 oxidation testing at 99° C. and 130° C.

Applying the modified Quantum® instrument, normal 20-g grease test samples were run in ASTM D942 for 100-hour periods, additionally, in some cases, 200-hour periods, depending upon the response at one hundred hours. Results on five of the six greases tested are shown in the Table below. For each test, pressure change with time was continuously recorded. As seen in FIG. 2, Grease A, a bio-based soy grease with an aluminium-compound thickener, was subjected to a 100-hour oxidation exposure under ASTM D942 methodology and temperature-modified methodology (130° C.). Interestingly, final pressures in the chamber showed almost total Oxygen uptake by the grease during testing from the test chamber pressure dropping to about 20-psi atmospheric pressures. As would be expected, when Grease A was exposed to ASTM D942 oxidation conditions at an elevated temperature of 130° C. for the 100-hour period, the rate of oxidation was significantly faster as shown in FIG. 2. The fact that there was more Oxygen left after the pressure reached equilibrium suggested that the oxidation at the higher temperature was more efficient.

Figure 3:
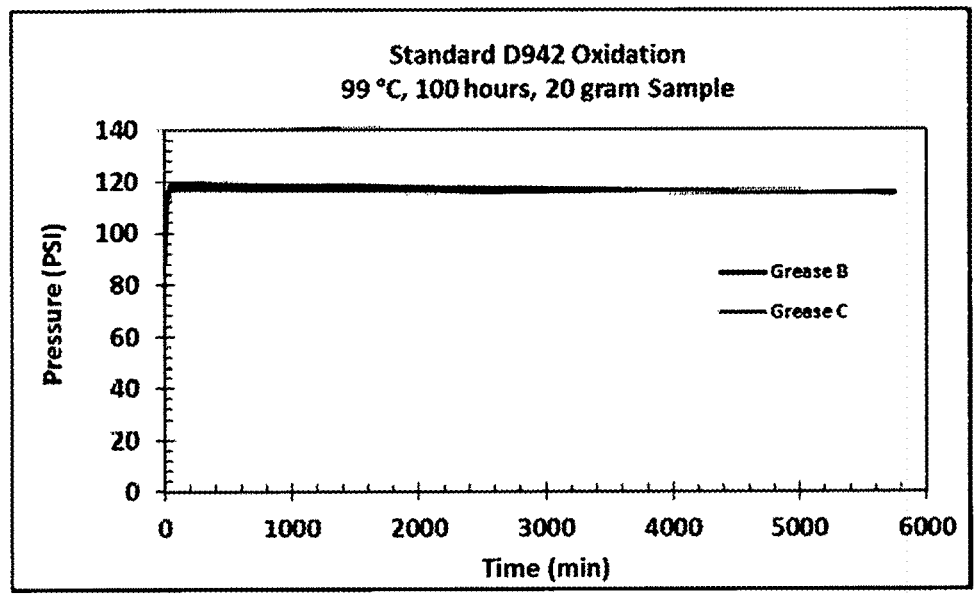
FIG. 3 is graph of Greases B and C, standard ASTM D942 oxidation testing at 99° C.

In contrast, as also shown in the Table, Grease B, another bio-based soy grease with an aluminium-additive thickener, and Grease C, a biodegradable synthetic ester grease with a lithium-additive thickener, were both found to be highly resistant to oxidation in this standard ASTM D942 test method. FIG. 3 shows the associated pressure-loss curves.

Greases B and C were found to have similar oxidative resistance to those of Greases E and F. Greases E and F samples were both mineral-based lithium-additive thickened grease found on the market with a similarly indicated application to automotive needs.

Figure 4:
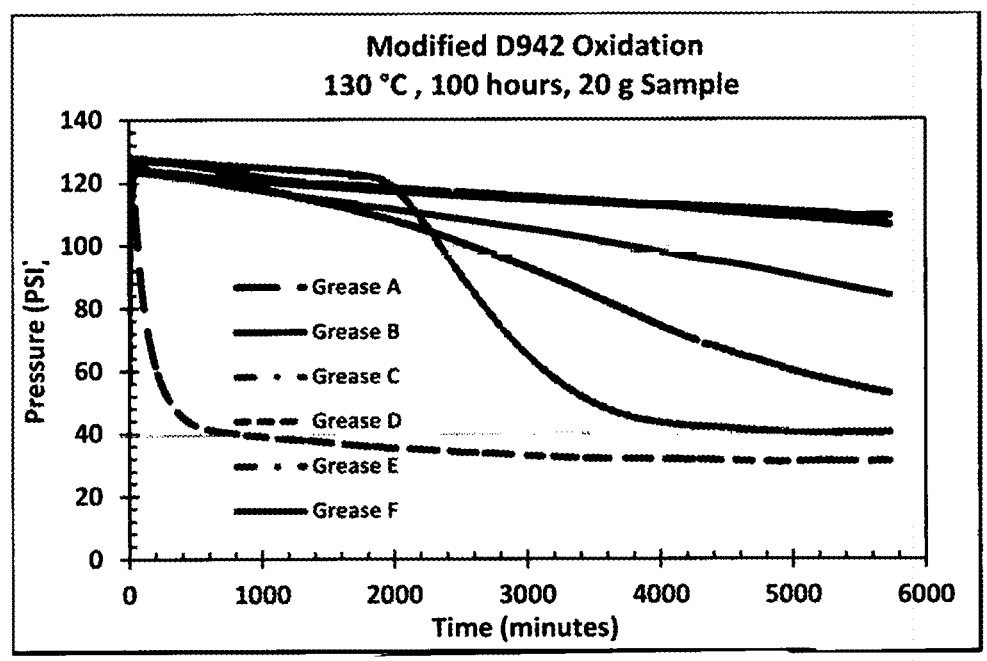
FIG. 4 is a graph of Greases A-F, ASTM D942 Oxidation Testing at 130° C.

As also shown in the Table, the oxidative resistance of the greases at an elevated temperature of 130° C. was evaluated. As indicated by the Oxygen pressure drop, the oxidation response increased from that at a lower temperature, as expected. However, the effect of the increased temperature of test was interestingly quite different among the greases, except for Grease A, which was already essentially fully oxidized at 100° C. The effect of an increase in test temperature from 100° C. to 130° C. is shown in FIG. 4. As shown, decreases in Oxygen pressure—and presumably concomitant increases in the degree of grease oxidation—range from 13.8 psi for Grease B to 83.4 psi for Grease C for the five greases tested at both temperatures. The two mineral oil-based greases, Greases E and F, show Oxygen pressure changes of 71.3 psi and 35.8 psi, respectively. Such results indicate that some greases are more susceptible to temperature change than others, irrespective of base oil source. This leads to the question of the appropriate temperature of test for a grease application as well as the question of the oxidation response of a grease over a reasonable temperature range.

TABLE

Oxidation Testing - Standard ASTM D942 and Modified ASTM D942 Testing

| Grease | Base Stock/ Thickener Additive | Recommended Operating Temperature Use Range for Grease | psi Drop (Temp. 99° C., 100-hour test, 20-g Sample) | psi Drop (Temp. 130° C., 100-hour test, 20-g Sample) | psi Drop (Temp. 99° C., 100-hour data, 2.5-g Sample) | psi Drop (Temp. 99° C., 200-hour data, 2.5-g Sample) |
|---|---|---|---|---|---|---|
| A | Bio (soy)/ Aluminum | 0° C.-215° C. | 97.0 | 87.9$^4$ | 51.6 | Not performed |
| B | Bio (soy)/ Aluminum | −30° C. 149° C. | 2.5 | 16.3 | 1.0 | 2.5 |

TABLE-continued

Oxidation Testing - Standard ASTM D942 and Modified ASTM D942 Testing

| Grease | Base Stock/ Thickener Additive | Recommended Operating Temperature Use Range for Grease | psi Drop (Temp. 99° C., 100-hour test, 20-g Sample) | psi Drop (Temp. 130° C., 100-hour test, 20-g Sample) | psi Drop (Temp. 99° C., 100-hour data, 2.5-g Sample) | psi Drop (Temp. 99° C., 200-hour data, 2.5-g Sample) |
|---|---|---|---|---|---|---|
| C | Synthetic ester/ Lithium | −40° C.-120° C. | 4.8 | 88.2[A] | 2.5 | 4.9 |
| D | Bio (canola)/ Aluminum | −23° C.-188° C. | Not performed | 21.8 | 1.7 | 3.0 |
| E | Mineral (Lithium Complex) | −23° C.-204° C. | 2.5 | 73.8[A] | 2.5 | 2.7 |
| F | Mineral (Lithium Complex) | −12° C.-163° C. | 5.7 | 41.5 | 1.9 | 3.7 |

[A]Varying degree of melting observed

Some limitations of the ASTM D942 method include its 20-g grease sample size, and the manner of exposure of the sample to a fixed volume of Oxygen during the test. In consideration of this, the effect of using 2.5 g of grease samples in this test (a thin layer of 0.5 g of grease in each of the five dishes) for either a 100-hour or a 200-hour time was conceived and explored.

This data is also shown in the Table. For example, Grease A showed a 51.6-psi drop in Oxygen pressure when the 2.5-g sample distributed evenly in live dishes (0.5-g sample per dish) was exposed to otherwise standard ASTM D942 conditions for a 100-hour test. Considering that the 2.5-g mass of grease employed with the present methodology is only one-eighth of that used in the ASTM 13942 test (20-g mass of grease evenly into five dishes), and the surface areas were substantially identical (an approximately 25-cm$^2$ exposed surface area of each of the five dishes, thus yielding an approximately 125-cm$^2$ total), the surface area to mass ratio was enhanced eight times (from approximately 6.25 cm$^2$/g to an approximately 50-cm$^2$/g value for the 5-dish, 2.5-g mass of grease—a 5-g sample evenly into five of these dishes having, an about 25-cm$^2$/g ratio), and the pressure drop as a percentage of test sample mass for the 2.5-g sample (20.6 psi/gram) was considerably greater than that obtained for the 20-g sample (4.9 psi/gram). This implies a greater extent of oxidation for the 2.5-g sample versus the 20-g sample for the same exposure duration, engendered through the enhanced, increased surface area to mass ratio of the sample.

Figure 5:
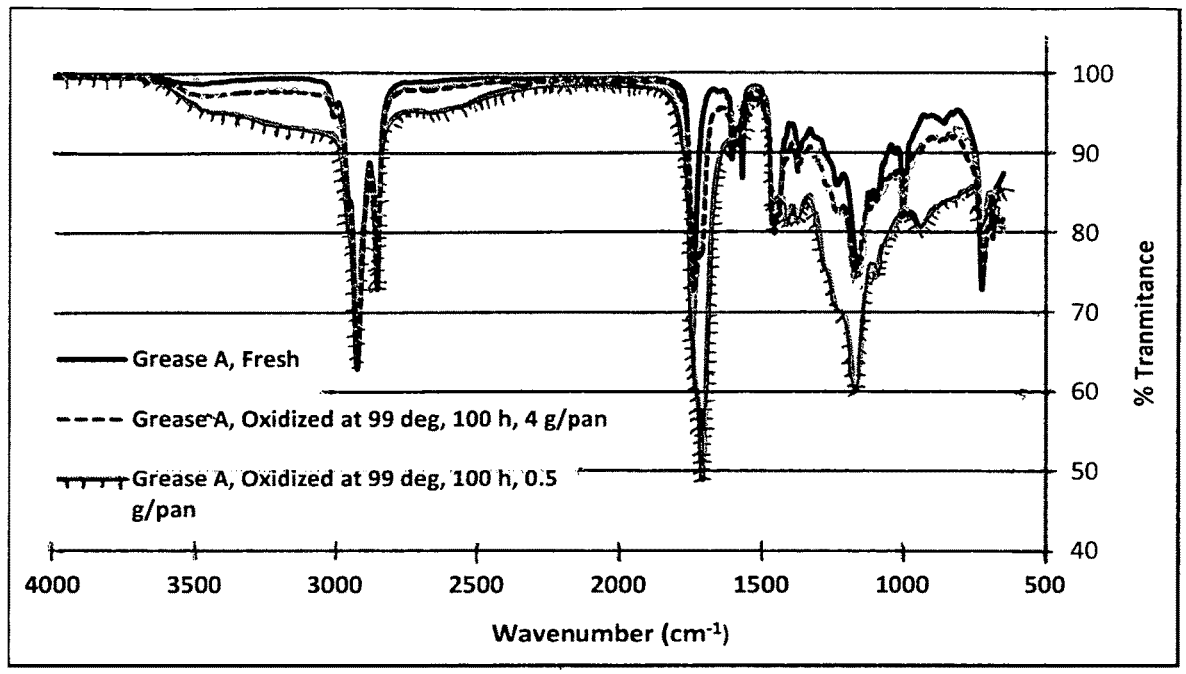
FIG. 5 is a graph of ATR-FTIR spectra as a combined plot of a sample of Grease A.

In another effort to improve the information gathered, ATR-FTIR analysis was employed. Comparison of the ATR-FTIR spectrograms of the 20-g and 2.5-g samples as in ASTM D942 tests on Grease A is shown in FIG. 5. For the 2.5-g sample, it is evident that at the wavenumbers between approximately 1700-1750 cm$^{-1}$, which are associated with carbonyl oxidation products such as those of carboxylic acids, ketones, aldehydes, and so forth, there is, as would be expected, a substantial increase as a consequence of more extensive oxidation.

As a result of this test comparison of Grease A, all other greases, which were found to exhibit good Oxygen resistance under standard ASTM D942 testing over a 100-hour period but appeared more unstable at 130° C. testing, were evaluated at a 2.5-g sample size, at 99° C. for a 200-hour duration, as shown in the Table. Under these test conditions, Greases B, C, E and F were found to respond somewhat similarly to the response of Grease A. That is, they show a somewhat greater pressure drop as a percentage of sample size for the 2.5-g samples relative to the standard 20-g samples, although the pressure drop for all five greases tested is quite small.

One of the perceived limitations of the ASTM D942 test method is the time it takes to evaluate very oxidation-resistant greases. Based on information obtained from members of ASTM Work Group #51938 at a Dec. 8, 2015 Work Group Meeting of ASTM D02 Petroleum Products and Lubricants in Austin, Tex., U.S.A., several users of ASTM D942 test methodology have reported running samples for one thousand hours and longer in cases of highly Oxygen resistant greases. Based on the present findings, however, a 2.5-g test sample could dramatically reduce the time required to assess the oxidative resistance of such greases.

ADDITIONAL WORK

Figure 6:
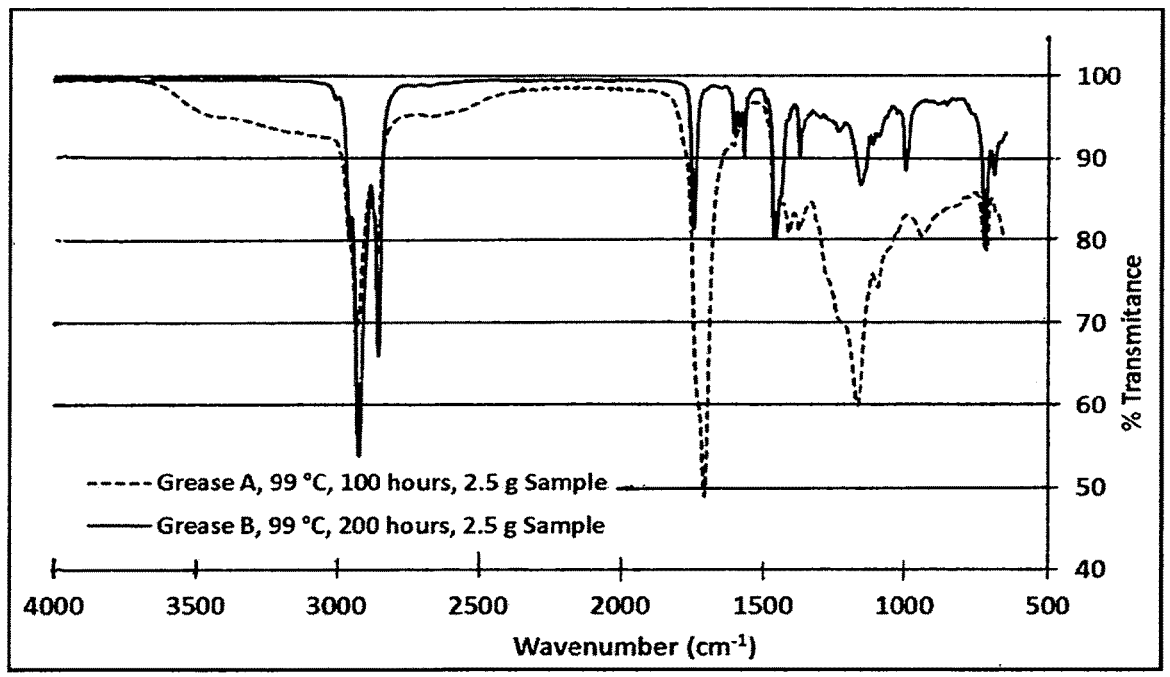
FIG. 6 is a graph of ATR-FTIR spectra comparing samples of Grease A with Grease B, taken in conjunction with another test protocol, a modified falex pin and vee block testing of the greases with present methodology.

A new method employing a modified falex pin and vee block test unit was used to test Grease A and Grease B for wear resistance. The present methodology was employed to test a 2.5-g sample of each grease with 0.5-g in each sample dish. ATR-FTIR spectra were taken of the grease samples, Grease A at 99° C. for a 100-hour period, and Grease B at 99° C. for a 200-hour period. The spectra are displayed in FIG. 6.

EPILOGUE

On the basis of the present discoveries, the ASTM D942 method could be extended to include other operational temperatures and a different test sample size, or a completely new method for assessing the oxidative resistance of a grease should be considered employing essential feature(s) hereof. Simple elevation of the test temperature resulted in accelerating the rate of oxidation, thus reducing one of the drawbacks of the ASTM D942 test method—testing duration—but depending upon the oxidative resistance the 20-g sample, it still may not fully oxidize in a reasonable test time owing to the fixed volume of Oxygen-to-sample ratio. On the other hand, reducing the test sample size and maintaining the same fixed volume of Oxygen, while heating at 99° C. as per ASTM D942, or at an elevated temperature, would reduce the overall test duration and provide greater insight into the oxidative stability of highly oxidative resistance grease formulations. The reduction in both sample size and test time would be beneficial in assessment of new additives and new grease formulations.

Thus, there is presented a significant new area of discovery or invention based on a fundamental experimental findings, i.e., the finding that a smaller grease sample, for example, a 2.5-g sample distributed equally into five test dishes and spread evenly and completely therein, oxidizes efficiently to a more complete extent in the Quantum® instrument with an ASTM D942 method, modified according to considerations of the smaller sample size, than a 20-g sample oxidizes per the standard ASTM D942 test method; and the finding that changing temperature from the 99° C. standard used in the ASTM D942 method can be beneficial and provide useful insight. Compare with the parent, noting the grease testing per ASTM D942 with the metal sleeve insert and the rack to hold the five glass dishes.

CONCLUSION TO THE INVENTION

The present invention is thus provided. Various feature(s), part(s), step(s), subcombination(s) and/or combination(s) can be employed with or without reference to or order of other feature(s), part(s), step(s), subcombination(s) and/or combination(s) in the practice of the invention, and numerous and sundry adaptations can be effected within its spirit, the literal claim scope of which is particularly pointed out by the following claims:

What is claimed is:

1. A method for testing a sample of grease or another organic paste product by contact with and exposure of said sample to Oxygen under pressure through use of a bomb vessel and an infrared spectrophotometer, which comprises carrying out the following steps (A-H), which are not required to be conducted in series unless noted otherwise:
   (A) providing said bomb vessel, which has a hollow interior;
   (B) providing at least one sample dish, wherein the at least one sample dish has a bottom and an enclosing member attached to and elevated above the bottom;
   (C) providing said sample to the at least one sample dish, wherein said sample is received and contained in the at least one sample dish has a mass, and a surface, wherein the surface is spaced apart from the bottom of the at least one sample dish and has associated therewith an area, wherein the surface directly contacts Oxygen when Oxygen is provided to the hollow interior of the bomb vessel; and supplying the at least one sample dish provided with said sample to the hollow interior of said bomb vessel, wherein said sample provided to the hollow interior of said bomb vessel has a direct Oxygen-contacting surface area to mass ratio of about 25 $cm^2$/gram or greater;
   (D) providing the Oxygen, under pressure greater than atmospheric pressure, to the interior of said bomb vessel, directly contacting said direct Oxygen-contacting surface of said sample with the Oxygen;
   (E) providing the infrared spectrophotometer, which is an FTIR device;
   (F) heating the interior of said bomb vessel containing said sample and at least initially the Oxygen, under said pressure greater than atmospheric pressure, to a predetermined temperature for a predetermined time;
   (G) following expiration of the predetermined time in step F, subjecting at least part of said sample to infrared spectrophotometric analysis by operating the infrared spectrophotometer and providing infrared spectral information concerning said sample; and
   (H) providing an analytical device that measures change of gaseous Oxygen pressure in the hollow interior of said bomb vessel, and measuring any change of the gaseous Oxygen pressure in the hollow interior of said bomb vessel by said analytical device.

2. The method of claim 1, wherein said direct Oxygen-contacting surface area to mass ratio is about 50 $cm^2$/gram or greater.

3. The method of claim 1, wherein said sample is evenly distributed in a plurality of individual said sample dishes as the at least one said sample dish such that said sample is less than about 1 gram per individual said sample dish.

4. The method of claim 2, wherein said sample is evenly distributed in a plurality of individual said sample dishes as the at least one said sample dish such that said sample is less than about 1 gram per individual said sample dish.

5. The method of claim 3, wherein said sample is evenly distributed in a plurality of individual said sample dishes as the at least one said sample dish such that said sample is about 0.5 gram or less per individual said sample dish.

6. The method of claim 4, wherein said sample is evenly distributed in a plurality of individual said sample dishes as the at least one said sample dish such that said sample is about 0.5 gram or less per individual said sample dish.

7. The method of claim 1, wherein the predetermined temperature of the heating step is about 110° C. or more.

8. The method of claim 2, wherein the predetermined temperature of the heating step is about 110° C. or more.

9. The method of claim 3, wherein the predetermined temperature of the heating step is about 110° C. or more.

10. The method of claim 4, wherein the predetermined temperature of the heating step is about 110° C. or more.

11. The method of claim 5, wherein the predetermined temperature of the heating step is about 110° C. or more.

12. The method of claim 6, wherein the predetermined temperature of the heating step is about 110° C. or more.

13. The method of claim 1, wherein the infrared spectrophotometer is an ATR-FTIR device.

14. The method of claim 2, wherein the infrared spectrophotometer is an ATR-FTIR device.

15. The method of claim 3, wherein the infrared spectrophotometer is an ATR-FTIR device.

16. The method of claim 4, wherein the infrared spectrophotometer is an ATR-FTIR device.

17. The method of claim 5, wherein the infrared spectrophotometer is an ATR-FTIR device.

18. The method of claim 6, wherein the infrared spectrophotometer is an ATR-FTIR spectral analysis device.

19. The method of claim 7, wherein the infrared spectrophotometer is an ATR-FTIR device.

20. The method of claim 1, wherein the predetermined temperature of the heating step is about 130° C.

21. A method for testing a sample of grease or another organic paste product by contact with and exposure of said sample to Oxygen under pressure through use of a bomb vessel and an infrared spectrophotometer, which comprises carrying out the following steps (A-H), which are not required to be conducted in series unless noted otherwise:
   (A) providing said bomb vessel, which has a hollow interior, wherein said bomb vessel is a rotatable bomb vessel held in a pivotable framework;

(B) providing at least one sample dish, wherein the at least one sample dish has a bottom and an enclosing member attached to and elevated above the bottom;

(C) providing said sample to the at least one sample dish, wherein said sample is received and contained in the at least one sample dish has a mass, and a surface, wherein the surface is spaced apart from the bottom of the at least one sample dish and has associated therewith an area, wherein the surface directly contacts Oxygen when Oxygen is provided to the hollow interior of the bomb vessel; and supplying the at least one sample dish provided with said sample to the hollow interior of said bomb vessel, wherein said sample provided to the hollow interior of said bomb vessel has a direct Oxygen-contacting surface area to mass ratio of about 25 $cm^2$/gram or greater;

(D) providing the Oxygen, under pressure greater than atmospheric pressure, to the interior of said bomb vessel, directly contacting said direct Oxygen-contacting surface of said sample with the Oxygen;

(E) providing the infrared spectrophotometer, which is an FTIR device;

(F) heating the interior of said bomb vessel containing said sample and at least initially the Oxygen, under said pressure greater than atmospheric pressure, to a predetermined temperature for a predetermined time;

(G) following expiration of the predetermined time in step F, subjecting at least part of said sample to infrared spectrophotometric analysis by operating the infrared spectrophotometer and providing infrared spectral information concerning said sample; and (H) providing an analytical device that measures change of gaseous Oxygen pressure in the hollow interior of said bomb vessel, and measuring any change of the gaseous Oxygen pressure in the hollow interior of said bomb vessel by said analytical device.

* * * * *